United States Patent [19]

Burrow et al.

[11] 4,148,732

[45] Apr. 10, 1979

[54] BACTERIA FILTER UNIT

[76] Inventors: Clovis E. Burrow, 8715 E. 146st St.; Flois D. Burrow, Rte. 4, Box 272, both of Noblesville, Ind. 46060

[21] Appl. No.: 924,194

[22] Filed: Jul. 13, 1978

Related U.S. Application Data

[63] Continuation of Ser. No. 784,679, Apr. 5, 1977, abandoned.

[51] Int. Cl.$^2$ ............................................. B01D 25/04
[52] U.S. Cl. ..................................... 210/232; 55/502; 55/503; 55/506; 55/509; 210/445; 210/446
[58] Field of Search ............... 210/445, 446, 450, 232, 210/493, 489; 55/498, 502–510; 21/94

[56] References Cited

U.S. PATENT DOCUMENTS

| | | | |
|---|---|---|---|
| 2,784,781 | 3/1957 | Rhoades | 55/DIG. 31 |
| 3,844,895 | 10/1974 | Rose et al. | 210/445 |
| 3,932,153 | 1/1976 | Byrns | 210/446 |
| 3,954,625 | 5/1976 | Michalski | 210/445 |

*Primary Examiner*—Frank Sever
*Attorney, Agent, or Firm*—Wallace E. Weakley

[57] ABSTRACT

A bacterial filter unit for use in anesthesia applications and respiratory procedures, which bacterial filter unit comprises a two-piece molded housing, each piece being of a generally frusto-conical shape and having an interlocking edge for joining the two housing pieces together in a sealing locking engagement, for retention of a filter media formed of fiberglas or other material between the two housing portions, and for sealing the filter media, each housing portion further having a tubular opening at the peak of the frusto-conical portion for connecting the filter unit in the necessary conduit in the anesthesia or respiratory application apparatus for filtering the bacteria passing through the lines.

3 Claims, 4 Drawing Figures

BACTERIA FILTER UNIT

This is a continuation of application Ser. No. 784,679, filed Apr. 5, 1977, now abandoned.

BACKGROUND OF THE INVENTION

1. Field of the Invention

The present invention relates to a bacteria filter unit for use in anesthesia application or other respiratory procedure, which filter unit has a two-piece housing, with said housing being formed with a unique sealing interlock means for locking the two portions of the housing together in sealing relationship and retaining a bacteria filter media between the two housing portions by means of the sealing interlock.

2. Description of the Prior Art

Many different bacteria filter devices are presently on the market. The various filter units and devices available today use many different types of filter media. However, the majority of the bacteria filter units in use in the medical field today are complicated, costly to manufacture, and expensive to use.

Most bacteria filter units are of at least a two-part construction, with the two parts being assembled together after the filter media has been installed within the two parts or attached to one of the parts of the filter unit. The two portions of the filter unit are usually joined together by engaging threads formed on the two parts of the filter body, or are glued or welded together in some manner, such as hot glue, ultrasonic welding or other method.

Each of these methods of assembly are quite expensive and do not always produce satisfactory results. Problems of leakage and high costs of assembly are presented.

Another problem area presented by the present filter units available on the market today occurs in those filter units which are designed to be conductive. Many times good conductivity is difficult to obtain between the various parts of the filter unit after the components are assembled together, due to the fact that the filter media sometimes acts as an insulator between the components of the filter unit. In addition, when hot glue or other sealing material is used, the sealing material often times acts as an insulator between the components.

SUMMARY OF THE INVENTION

The present invention overcomes the many disadvantages of the prior art bacteria filter devices by presenting a simple filter unit design and structure that is inexpensive to manufacture and assemble, and which utilizes a simple, yet highly effective filter media.

The filter media employed by the present invention, when used in combination with the filter unit of the present invention, filters the bacteria from the fluid flow by means of impaction, inertia, electrostatic charge and by a tortuous path.

The present invention presents a unique interlocking and sealing construction that is inexpensive to manufacture, yet is simple and easy to assemble, and is effective to retain the filter media within the housing and obtain a sealing relationship between the two housing pieces.

The present invention presents a method of and structure for assembling a bacteria filter unit in a simple, efficient manner, without requiring the use of additional tools, or employing other sealing means, such as hot glue, ultrasonic welding, or other means.

The present invention presents a unique seal and interlock design for use in joining two portions of a bacteria filter unit together in sealing relationship with each other without requiring the use of additional sealing means.

The present invention further presents a unique seal and interlock design which obtains good conductivity between the two parts of the filter unit housing, to enable good conductivity to be obtained in the circuit in which the filter unit is located without requiring any additional electrical connections.

These and other advantages of the present invention will be seen upon reading the description of the Preferred Embodiments of the subject invention, contained in the following specification and viewing the drawings, which form a part of this application.

DESCRIPTION OF THE PREFERRED EMBODIMENTS

A description of the preferred embodiments of the subject invention will now be set forth with reference to the drawings.

Figure 1:
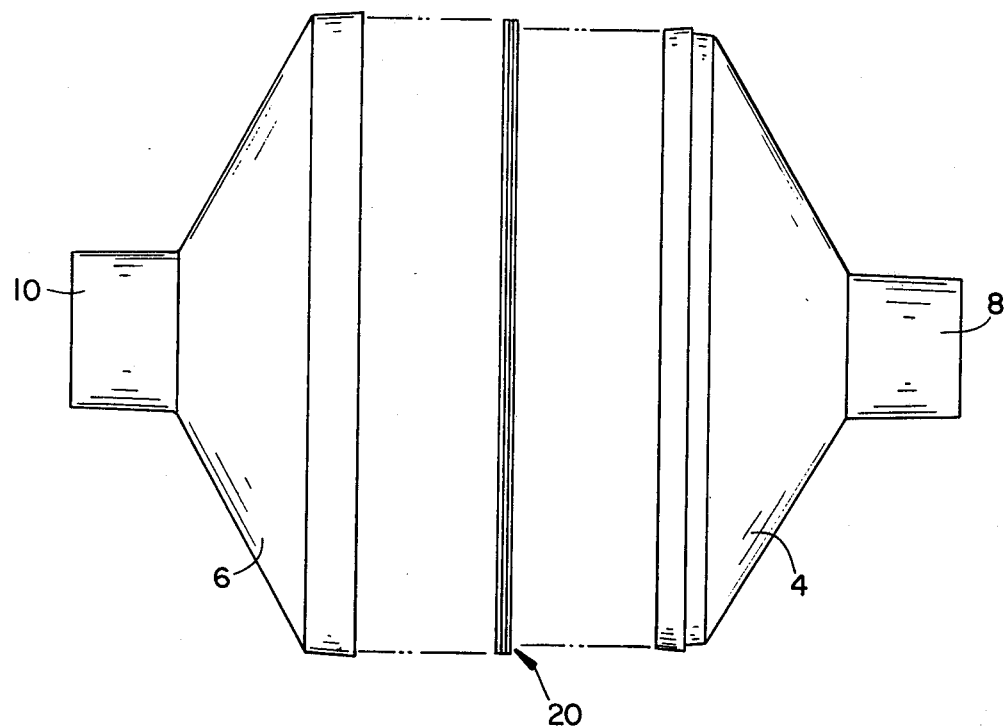
FIG. 1 is a view of the unassembled components showing the relationship of the components of the subject invention prior to assembly.
Figure 2:
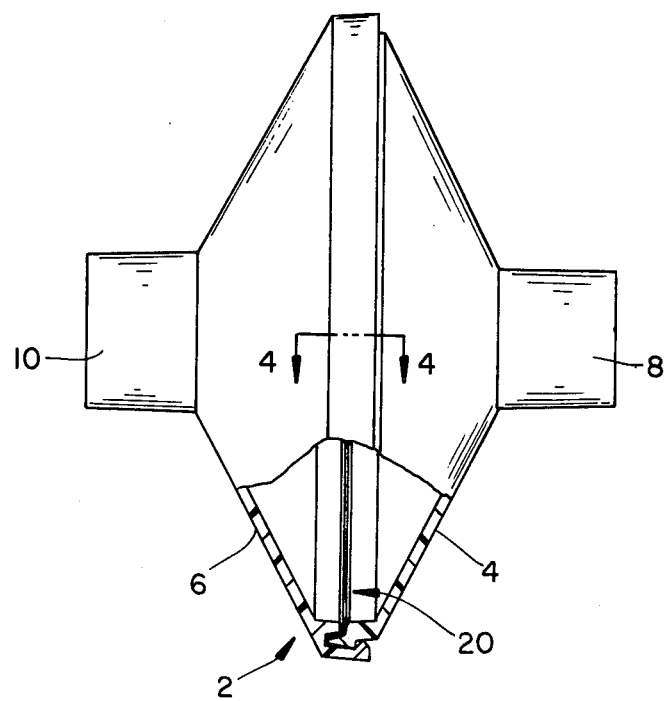
FIG. 2 is a partial cutaway view of the subject invention in its assembled form.

Referring now to FIGS. 1 and 2 of the drawings, the bacteria filter unit assembly 2 is comprised of two caps or end enclosing portions 4 and 6. The end enclosure portions or caps 4 and 6 according to the present invention are of a generally frusto-conical configuration as shown in the drawings, although the general shape of the end portions 4 and 6 may be of any desired configuration. Each of the end portions 4 and 6 have tubular extensions 8 and 10, respectively, extending from the outermost end thereof. The tubular extentions 8 and 10 are hollow and connect with an opening through the ends of the end portions 4 and 6 for interconnecting the filter assembly 2 into a suitable fluid conduit. The interconnection within the conduit may be by any suitable means, such as by friction fit, hose clamps, or other suitable means.

Figure 3:
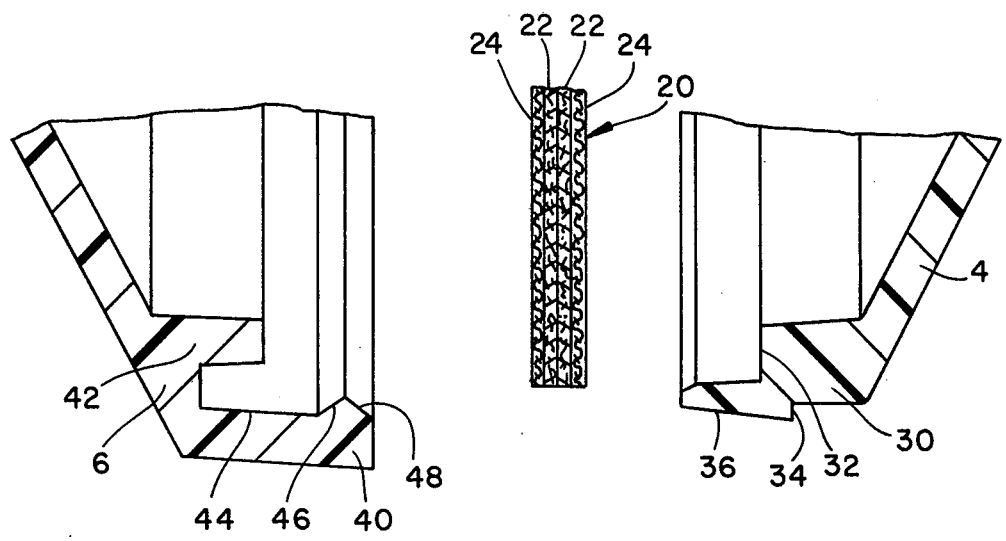
FIG. 3 is an exploded view of the cutaway portion of FIG. 2 showing the components of the subject invention in their unassembled relationship; and, FIG. 4 is an exploded view of the cutaway portion of FIG. 2, showing the components of the subject invention in their assembled relationship.
Figure 4:
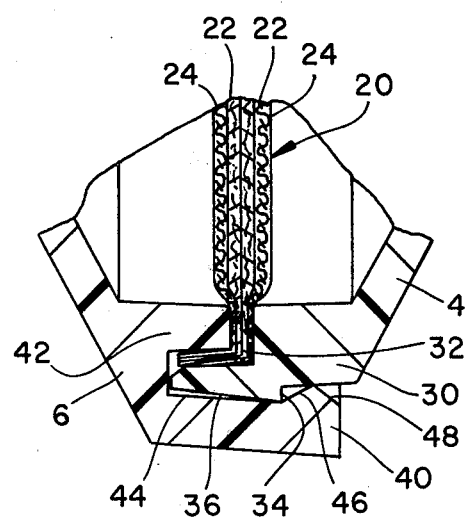

As may be more readily seen in FIGS. 3 and 4, one end portion 4 is formed with a male sealing and interlocking flange or lip 30. The other end portion or cap 6 is formed with a female sealing and interlocking flange or lip 40. The flanges 30 and 40 are adapted to be interlocked into sealing engagement with each other, as will be more particularly described herein below.

The male interlocking flange or lip 30 formed on end cap 4 extends from the outer periphery of the frusto-conical end portion 4, as may be readily seen by viewing FIG. 3. The male interlock flange or lip 30 has a shoulder 32 formed about the inner pheriphery thereof, as shown in detail in FIG. 3. This inner shoulder 32 is adapted to retain a filter media 20 within the filter unit assembly 2, as shown in FIG. 4 of the drawings. The assembly of the components of the subject invention will be explained in further detail in the following disclosure.

Referring further to FIGS. 3 and 4, the male interlocking flange or lip 30 of the end cap or cover 4 also has a stepped shoulder 34 formed on the outer surface thereof and extending radially outwardly for engaging a corresponding lip formed on the female interlocking flange of the female end portion 6, as shown in further detail in FIG. 4 and described hereinafter. The outer surface 36 of the male interlocking flange or lip 30 tapers inwardly from the outer edge of the stepped shoulder 34, as shown in detail in FIGS. 3 and 4, to assist in the assembly of the components of the subject invention.

The female end portion or cap 6 of the filter housing assembly 2 has an outer interlocking wall or flange 40 extending circumferentially from the outer edge of the frusto-conical end portion 6 in a cylindrical manner, as seen in detail in FIG. 3. The inside diameter of the outer wall or flange 40 is slightly smaller than the outer-most diameter of the male interlocking flange or lip 30 of the male end portion 4, as may be more readily seen by viewing FIG. 4.

As shown in FIG. 3, the outer wall 40 of the female end portion 6 has an inwardly projecting shoulder 46 formed around the inner periphery thereof at its outer end. The outer locking lip 46 is adapted to engage the stepped shoulder 34 on the outer surface of the male sealing lip or flange 30, and engage in contact with the outer surface of the male lip or flange 30 in sealed relationship therewith, as shown in detail in FIG. 4 of the drawings, and described hereinbelow.

An inner wall 42 is formed around the periphery of the female end portion or cap 6 in spaced-apart relationship to the outer wall or flange 40, resulting in a groove 44 being formed between the outer wall 40 and inner 42. This specific structure is shown in FIGS. 3 and 4. The height of the wall 42 is less than the overall height of the outer wall 40, with the dimension of the wall 42 of the female end portion or cap 6 being such that its end surface extends approximately to the surface of the stepped shoulder 32 of the male flange 30 when the end caps 4 and 6 are interlocked with each other. This specific configuration is shown in detail in FIG. 4 of the drawings. The purpose of the inner wall 42 is to provide an abuttment for clamping the filter 20 within the housing portions 4 and 6 of the filter unit and obtain an effective retention of the filter pad 20 about its entire periphery, so that 100% filtration of the fluid passing through the filter unit 2 can be obtained.

In addition to clamping the filter pad 20 against the stepped shoulder 32 of the male flange 30, the inner wall 42 of the female end portion or cap 6 presents a surface against which the inner surface of the male flange 30 engages to obtain an effective seal in the interlocking connection between the end portions 4 and 6 of the filter assembly 2. The details of the sealing contact and clamping action are shown in FIG. 4, with the overall relationship of the components of the subject invention being shown in FIG. 2 of the drawings.

Referring now to FIGS. 1, 3 and 4, the filter media 20 used in the structure according to the subject invention is comprised of four layers. The two inner layers 22 are formed of the actual filter material, which, in the case of the present invention, is fiberglas. The two inner layers of fiberglas mat material 22, comprising the actual filter material, are held between and retained by two outer layers 24 formed of a non-woven material. Tests have shown that the use of a filter media 20 having the construction described hereinabove and shown in the subject drawings, in combination with the structure and design of the filter unit according to the present invention results in a highly efficient filter unit. The filter media or filter pad 20 achieves filtration by means of impaction, inertia, electrostatic charge, and by presenting a tortuous path to the travel of the bacteria, which results in an effective filtering of the bacteria from the fluid flow.

As shown in FIG. 1, the filter media or pad 20 is aligned between the end portions or caps 4 and 6. In actual design, the filter pads 20 have an outer diameter or peripheral shape which corresponds to the inner diameter or peripheral dimension of the outer wall 40 of the female locking flange or lip on the end cap 6. This dimension corresponds generally to the outer peripheral dimension of the outer surface 36 of the male interlocking flange or lip 30. The filter media or pad 20 is placed on the inner wall 42 of the female end portion of cap 6, and the male lip 30 of the filter end portion 4 is inserted and pressed into the slot or groove 44 formed between the outer wall 40 and the inner wall 42 of the female seal interlock. The two end portions or caps 4 and 6 are pressed together to cause the outer-most edge of the male lip 30 to press the outer edge of the filter media 20 around the end of the inner wall 42 of the female interlock, as shown in detail in FIG. 4 of the drawings. The outer edge of the filter pad 20 is clamped between the stepped shoulder 32 of the male lip 30 and the end of the inner wall 42 or the female interlocking flange. In addition, the edge of the filter pad 20 is trapped and sealed between the outer surface of the inner wall 42 of the female interlock and the inner surface of the male lip 30. This clamping action is effective around the entire periphery of the filter media or pad 20, thereby resulting in 100% of the fluid passing through the filter unit passing through the filter media also, thereby obtaining 100% filtration of the fluid passing through the filter assembly 2.

Referring further to FIG. 4, when the male flange 30 is forced into the slot or groove 44 between the inner and outer walls 40 and 42 of the female locking flange assembly, the outer locking lip 46 on the inner circumference of the wall 40 of the female seal and interlock flange engages the stepped shoulder 34 formed on the outer surface of the male locking lip 30. This engagement effectively locks the male interlock and seal flange or lip 30 within the groove 44 and simultaneously forms an effective seal between the end portions or units 4 and 6 around the entire periphery of the joint.

The components of the present invention are formed of any suitable type of plastic by an injection molding process. However, any suitable type of production process and suitable material can be used to manufacture the subject invention. If desired, suitable material having electrically conductive characteristics can be added to the filter unit material, thereby resulting in a filter unit that is electrically conductive. Furthermore, any suitable filter media can be employed in the subject filter unit assembly, depending upon the actual application and use of the subject unit assembly. The use and application of the subject invention is not limited specifically to bacteria filter applications, but may be used in any filtering application without varying from the scope of the present invention.

What is claimed is:

1. A bacteria filter unit comprising in combination a first housing portion and a second housing portion, a filter media adapted to be interposed between said first and second housing portions in sealed relationship therewith, a female locking and gas sealing means formed around the periphery of one end of said first housing portion, a gas conduit connecting means formed on the other end of said first housing portion, said female locking and gas sealing means having an outer wall flange and an inner wall flange extending from the peripheral edge of said one end of said first housing portion, said inner and outer wall flanges being parallel to each other in spaced-apart relationship, said outer wall flange extending from said first housing portion a greater distance than said inner wall flange, said outer wall flange having an inwardly projecting lip formed around the inner periphery thereof above the outer end of said inner wall flange, a male locking and gas sealing means formed around the periphery of one end of said second housing portion, a gas conduit connecting means formed on the other end of said second housing portion, said male locking and gas sealing means comprising a shouldered flange extending from the peripheral edge of said one end of said second housing portion in parallel relationship with the inner and outer wall flanges of said female locking and gas sealing means, said shouldered flange of said male locking and gas sealing means having a first stepped shoulder formed around the inner periphery thereof, the dimension from the end surface of said flange to said inner stepped shoulder of said male locking and gas sealing means generally corresponding to the height of said inner wall of said female locking and gas sealing means, and a second shoulder formed on the outer periphery of said flange of said male locking and gas sealing means, the dimension from the end surface of said flange to said outer shoulder thereon corresponding to the dimension from the bottom of the groove between the inner and outer walls of said female locking and gas sealing means to the lip formed on the inner surface of said outer wall of said female locking and gas sealing means, said filter media having a peripheral dimension corresponding generally to the peripheral dimension of the inner surface of the outer wall flange of said female locking and gas sealing means, whereby, upon engagement of said flange of said male locking and gas sealing means within the groove between said inner and outer wall flanges of said female locking and gas sealing means, said filter media is retained between the end surface of said inner wall of said female locking and gas sealing means and said inner stepped shoulder of said flange of said male locking and gas sealing means and is tensioned by the movement of said shouldered flange of said male locking and gas sealing means into the space between the inner and outer wall flanges of said female locking and gas sealing means and said first housing portion and said second housing portion are locked together in sealing relationship with each other by the engagement of said male locking and gas sealing means within said female locking and gas sealing means.

2. A bacteria filter unit as set forth in claim 1, wherein said female locking and gas sealing means further comprises a beveled edge surface formed on the inner edge of said outer wall flange and said male locking and gas sealing means further comprises a tapered surface formed on the outer edge surface of said flange, said tapered surface of said male locking and gas sealing means adapted for engagement with said beveled edge surface on the outer wall of said female locking and gas sealing means to assist in assembly of the first and second housing portions of said bacteria filter unit.

3. A bacteria filter unit comprising in combination a first housing portion and a second housing portion, a filter media adapted to be interposed and locked between said first and second housing portions in sealed relationship therewith, a female locking and gas sealing means formed around the periphery of one end of said first housing portion, a gas conduit connecting means formed on the other end of said first housing portion, said female locking and gas sealing means having an outer wall flange and an inner wall flange extending from the peripheral edge of said one end of said first housing portion, said inner and outer wall flanges being parallel to each other in spaced-apart relationship, said outer wall flange extending from said first housing portion a greater distance than said inner wall flange, said outer wall flange having an inwardly projecting lip formed around the inner periphery thereof above the outer end of said inner wall flange, said inwardly projecting lip having an outwardly tapering surface on the outermost edge thereof, a male locking and gas sealing means formed around the periphery of one end of said second housing portion, a gas conduit connecting means formed on the other end of said second housing portion, said male locking and gas sealing means comprising a shouldered flange extending from the peripheral edge of said one end of said second housing portion in parallel relationship with the inner and outer wall flanges of said female locking and gas sealing means, said shouldered flange of said male locking and gas sealing means having a first stepped shoulder formed around the inner periphery thereof and a second shoulder formed on the outer periphery thereof, the distance between said inner stepped shoulder and said outer stepped shoulder on the flange of said male locking and gas sealing means plus the thickness of said filter media being greater than the distance between the end surface of said inner wall flange and the inwardly projecting lip formed on the inner periphery of said outer wall flange of said female locking and gas sealing means to provide a combined lock and seal upon engagement of the shouldered flange of said male locking and gas sealing means within the groove between the inner and outer wall flanges of said female locking and gas sealing means, the outer surface of said shouldered flange of said male locking and gas sealing means being tapered inwardly from the outer stepped shoulder thereon, the outside diameter of the outermost end of the flange of said male locking and gas sealing means plus the thickness of said filter media being equal to the inside diameter of the outer wall flange of said female locking and gas sealing means, the inside diameter of said shouldered flange of said male locking and gas sealing means being equal to the outside diameter of said inner wall flange of said female locking and gas sealing means, whereby, upon engagement of said shouldered flange of said male locking and gas sealing means within the groove between said inner and outer walls of said female locking and gas sealing means, said filter media is tensioned across the end surface of said inner wall of said female locking and gas sealing means and is bent at right angles and compressed between the inner wall flange of said female locking and gas sealing means and the shouldered flange and first stepped shoulder of said male locking and gas sealing means to lock said first and second housing portions together and provide a gas seal around the periphery of said filter media between said first and second housing portions.

* * * * *